United States Patent
Leem et al.

(10) Patent No.: US 10,281,412 B2
(45) Date of Patent: May 7, 2019

(54) APPARATUS FOR MEASURING SEMICONDUCTOR DEVICE

(71) Applicant: Samsung Electronics Co., Ltd., Suwon-si, Gyeonggi-do (KR)

(72) Inventors: Choon-Shik Leem, Seoul (KR); Yeon-Joong Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 436 days.

(21) Appl. No.: 15/203,070

(22) Filed: Jul. 6, 2016

(65) Prior Publication Data

US 2017/0102343 A1    Apr. 13, 2017

(30) Foreign Application Priority Data

Oct. 8, 2015    (KR) .................... 10-2015-0141332

(51) Int. Cl.
*G01N 23/20025*    (2018.01)

(52) U.S. Cl.
CPC . *G01N 23/20025* (2013.01); *G01N 2223/052* (2013.01); *G01N 2223/6116* (2013.01)

(58) Field of Classification Search
USPC ................ 250/310, 306, 307, 442.11
See application file for complete search history.

(56) References Cited

U.S. PATENT DOCUMENTS

| | | | | |
|---|---|---|---|---|
| 5,029,250 A | * | 7/1991 | Komatsu ............... | G01B 15/04 250/307 |
| 5,866,904 A | * | 2/1999 | Todokoro .............. | G01B 15/00 250/307 |
| 8,766,185 B2 | * | 7/2014 | Shimakura ............ | H01J 37/04 250/306 |
| 2007/0120056 A1 | * | 5/2007 | Nagatomo ............ | B82Y 10/00 250/310 |

FOREIGN PATENT DOCUMENTS

| | | |
|---|---|---|
| JP | 2006-313680 | 11/2006 |
| JP | 2008-282761 | 11/2008 |
| KR | 102007-0032479 | 3/2007 |

* cited by examiner

*Primary Examiner* — Kiet T Nguyen
(74) *Attorney, Agent, or Firm* — Myers Bigel, P.A.

(57) ABSTRACT

An apparatus for measuring a semiconductor device includes a beam irradiating unit configured to irradiate a first beam to a semiconductor substrate, a stage configured to receive the semiconductor substrate thereon and which is configured to rotate toward a central axis, which is perpendicular to a horizontal plane lying in the same plane with the semiconductor substrate, by a first angle to the horizontal plane and a second angle that is different from the first angle, a detector configured to receive a second beam generated by reflecting the first beam to the semiconductor substrate at the first angle and to receive a third beam generated by reflecting the first beam to the semiconductor substrate at the second angle, and an arithmetic operation unit configured to generate a 3D image of the semiconductor substrate using the second beam and the third beam received by the detector.

15 Claims, 16 Drawing Sheets

APPARATUS FOR MEASURING SEMICONDUCTOR DEVICE

This application claims priority from Korean Patent Application No. 10-2015-0141332 filed on Oct. 8, 2015, the disclosure of which is incorporated herein by reference in its entirety.

BACKGROUND

1. Technical Field

Example embodiments of the present inventive concept relate to an apparatus for measuring a semiconductor device.

2. Description of the Related Art

Generally, in research in the fields of physics, chemistry and materials, it is very important to measure optical properties of materials and measure thicknesses of thin films. In particular, various nano-thin film fabrication processes are being used in the semiconductor industry. To evaluate physical properties of fabricated nano-thin films, a non-destructive, non-contact, real-time measuring technology is being widely used.

In the semiconductor industry, a measurement region limited to an area of tens of μm× tens of μm is provided in a wafer in order to evaluate through measurement various thin-film fabrication processes for producing a semiconductor device. In addition, a technology of focusing on the surface of a sample placed in the measurement region is being used to measure physical properties of the measurement region.

SUMMARY

Example embodiments of the present inventive concept provide an apparatus for measuring the 3D structure of a semiconductor device in a non-destructive manner.

Example embodiments of the present inventive concept also provide an apparatus for measuring a semiconductor device, the apparatus comprising a stage for measuring the 3D structure of a semiconductor device in a non-destructive manner.

According to an example embodiment of the present inventive concept, an apparatus for measuring a semiconductor device is provided. The apparatus includes a beam irradiating unit configured to irradiatea first beam to a semiconductor substrate, a stage configured to receive the semiconductor substrate thereon and which is configured to rotate toward a central axis, which is perpendicular to a horizontal plane lying in the same plane with the semiconductor substrate, by a first angle to the horizontal plane and a second angle that is different from the first angle, a detector configured to receive a second beam generated by reflecting the first beam to the semiconductor substrate at the first angle and to receive a third beam generated by reflecting the first beam to the semiconductor substrate at the second angle, and an arithmetic operation unit configured to generate a 3D image of the semiconductor substrate using the second beam and the third beam received by the detector.

In some embodiments, the apparatus includes a stage driver having a spherical first end inserted into the stage and a second end disposed under the stage in a direction in which the central axis extends. The stage driver may be configured to rotate the stage toward the central axis by the first and second angles to the horizontal plane. The arithmetic operation unit may be configured to control the stage driver.

In some embodiments, the stage comprises a flat upper surface and a hemispherical lower surface and further comprising a stage driver adjacent a lower surface of the stage and that is configured to rotate the stage toward the central axis by the first and second angles to the horizontal plane. The stage driver may be configured to rotate the stage about the central axis on the horizontal plane.

In some embodiments, the apparatus includes an angle adjuster which lies in the horizontal plane and is positioned around a perimeter of a side surface of the stage and is connected to the stage so as to rotate the stage toward the central axis by the first and second angles.

In some embodiments, the apparatus includes a diffraction adjuster which lies in the same plane with the angle adjuster and is positioned around a perimeter of a side surface of the angle adjuster and is connected to the angle adjuster so as to rotate the stage about the central axis on the horizontal plane.

In some embodiments, the second and third beams comprise electrons, and the detector comprises an electrode which induces the electrons toward the detector.

According to an example embodiment of the present inventive concept, an apparatus for measuring a semiconductor device is provided. The apparatus includes a beam irradiating unit, and a measuring unit configured to measure a structure of a semiconductor pattern placed on a stage using first and second beams irradiated from the beam irradiating unit, wherein the measuring unit rotates the stage toward a central axis, which is perpendicular to a horizontal plane lying in the same plane with the stage, by a first angle to the horizontal plane, obtains a first measured value of the semiconductor pattern by irradiating the first beam to the semiconductor pattern, rotates the stage toward the central axis by a second angle different from the first angle to the horizontal plane, and obtains a second measured value of the semiconductor pattern by irradiating the second beam to the semiconductor pattern.

In some embodiments, the measuring unit comprises a detector configured to detect the first and second beams reflected by the semiconductor pattern to obtain the first measured value and the second measured value.

In some embodiments, the measuring unit comprising an arithmetic operation unit configured to generate a first calculated value using the first angle and the first measured value, to generate a second calculated value using the second angle and the second measured value, and to generate an actual value using a mean value of the first calculated value and the second calculated value. In some embodiments, the arithmetic operation unit obtains 2D images of the semiconductor pattern by combining a plurality of actual values and obtains a 3D image of the semiconductor pattern by combining the 2D images.

In some embodiments, the stage is configured to rotate on the same plane with the stage rotated by the first angle to the horizontal plane and is rotated on the same plane with the stage rotated by the second angle to the horizontal plane. The measuring unit may include an arithmetic operation unit configured to obtain a plurality of first calculated values using the first angle and a plurality of first measured values obtained by rotating the stage on the same plane with the stage at the first angle, to obtain a first mean value using the first calculated values, to obtain a plurality of second calculated values using the second angle and a plurality of second measured values obtained by rotating the stage on the same plane with the stage at the second angle, to obtain a second mean value using the second calculated values, and to calculate an actual value using the first mean value and the second mean value.

In some embodiments, an apparatus for measuring a semiconductor device is provided. The apparatus includes a beam irradiating unit configured to irradiate a beam to a semiconductor substrate that is reflected as a reflected beam from the semiconductor substrate; a stage configured to receive the semiconductor substrate thereon and configured to rotate toward a central axis, which is perpendicular to a horizontal plane lying in the same plane with the semiconductor substrate; a detector configured to detect the reflected beam from the semiconductor substrate; and an arithmetic operation unit configured to control a rotation of the stage such that two or more reflected beams are detected by the detector at two or more respective different angles.

In some embodiments, the arithmetic operation unit is configured to generate a 3D image of the semiconductor substrate using the two or more reflected beams detected by the detector. In some embodiments, the arithmetic operation unit is configured to generate two or more calculated values corresponding to the two or more reflected beams using the two or more respective different angles, and to generate an actual value using a mean value of the two or more calculated values. In some embodiments, the arithmetic operation unit obtains 2D images of the semiconductor pattern by combining a plurality of actual values and obtains a 3D image of the semiconductor pattern by combining the 2D images.

In some embodiments, the irradiated beam and the at least two reflected beams comprise electrons, and the detector comprises an electrode which induces the electrons toward the detector.

However, example embodiments of the present inventive concept are not restricted to the one set forth herein. The above and other aspects of the present inventive concept will become more apparent to one of ordinary skill in the art to which the present inventive concept pertains by referencing the detailed description of the present inventive concept given below.

BRIEF DESCRIPTION OF THE DRAWINGS

The above and other aspects and features of the present inventive concept will become more apparent by describing in detail example embodiments thereof with reference to the attached drawings, in which.

DETAILED DESCRIPTION OF THE EMBODIMENTS

Figure 1:
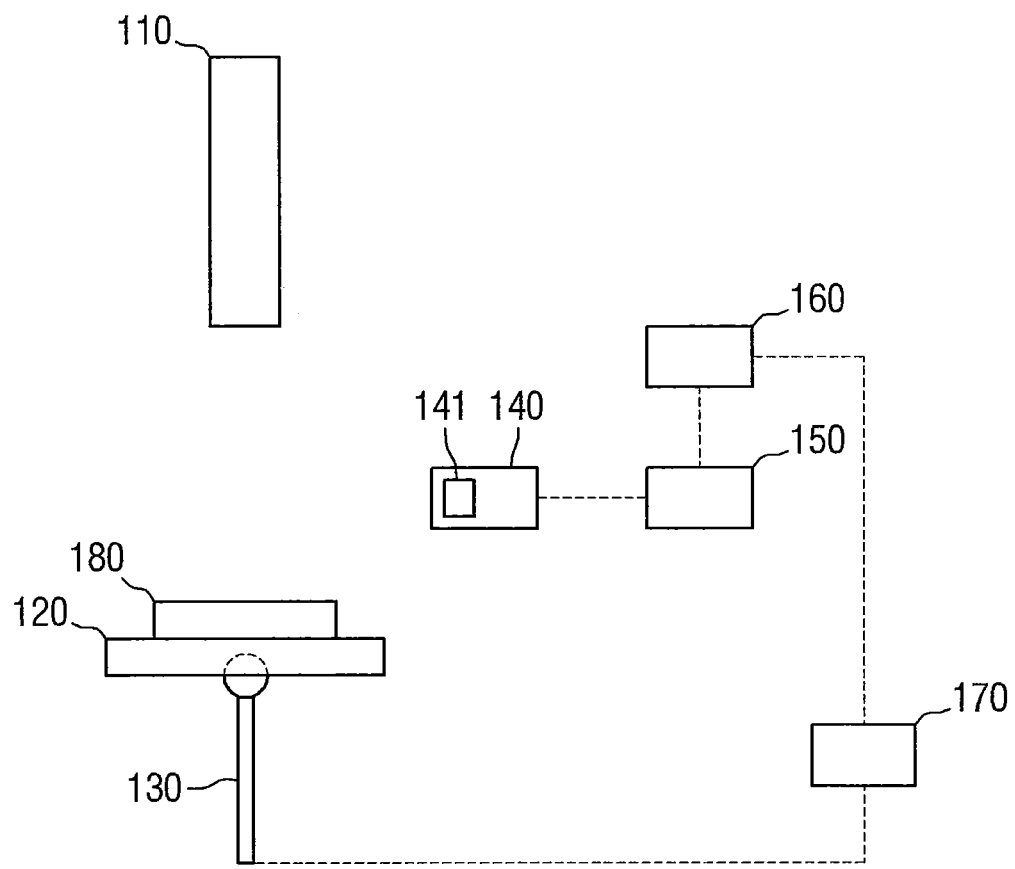
FIG. 1 is a schematic diagram of an apparatus for measuring a semiconductor device according to an embodiment of the present inventive concept.

Example embodiments of the present disclosure will be described more fully hereinafter with reference to the accompanying drawings. In the drawings, the size and relative sizes of layers and regions may be exaggerated for clarity. Like reference numerals may refer to like elements throughout the accompanying drawings.

It will be understood that when an element or layer is referred to as being "on," "connected to", or "covered by" another element or layer, it can be directly on, connected to, or covered by the other element or layer or intervening elements or layers may be present. In addition, it will also be understood that when an element or layer is referred to as being "between" two elements or layers, it can be the only element or layer between the two elements or layers, or one or more intervening elements or layers may also be present. As used herein, the term "and/or" includes any and all combinations of one or more of the associated listed items. Further, when two or more elements or values are described as being substantially the same as or equal to each other, it is to be understood that the elements or values are identical to each other, indistinguishable from each other, or distinguishable from each other but functionally the same as each other as would be understood by a person having ordinary skill in the art.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure.

The present disclosure will be described with reference to perspective views, cross-sectional views, and/or plan views, in which example embodiments of the disclosure are shown. Thus, the profile of an example view may be modified according to manufacturing techniques and/or allowances. That is, the example embodiments of the disclosure are not intended to limit the scope of the present disclosure but cover all changes and modifications that can be caused due to a change in manufacturing process. Thus, regions shown in the drawings are illustrated in schematic form and the shapes of the regions are presented simply by way of illustration and not as a limitation.

An apparatus for measuring a semiconductor device according to an embodiment of the present inventive concept will now be described with reference to FIG. 1.

FIG. 1 illustrates an apparatus 100 for measuring a semiconductor device according to an embodiment of the present inventive concept.

Referring to FIG. 1, the apparatus 100 for measuring a semiconductor device includes a beam irradiating unit 110 and a measuring unit. The measuring unit includes a stage 120, a stage driver 130, a detector 140, an electrode 141, an amplifier 150, an imaging unit 160, and an arithmetic operation unit 170.

The beam irradiating unit 110 may be placed above the stage 120. The beam irradiating unit 110 may irradiate a beam to a semiconductor substrate 180 placed on the stage 120.

The beam irradiating unit 110 may be, for example, a scanning electron microscope. In this case, the beam irradiating unit 110 may irradiate electrons to the semiconductor substrate 180.

The semiconductor substrate 180 may be a silicon substrate based on a semiconductor wafer. In some embodiments, the semiconductor substrate 180 may be a substrate for packages, such as a printed circuit board (PCB).

The semiconductor substrate 180 may include a semiconductor pattern having a 3D structure. For example, the semiconductor substrate 180 may include a plurality of fin structures.

The semiconductor substrate 180 may be, for example, a bulk silicon substrate. Otherwise, the semiconductor substrate 180 may be a silicon substrate or a substrate made of another material such as silicon germanium, indium antimonide, lead telluride, indium arsenide, indium phosphide, gallium arsenide or gallium antimonide. Alternatively, the semiconductor substrate 180 may include a base substrate and an epitaxial layer formed on the base substrate.

The stage 120 may be placed under the beam irradiating unit 110. The semiconductor substrate 180 may be placed on the stage 120.

The position and slope of the semiconductor substrate 180 can be changed by driving the stage 120 as described in greater detail herein.

The stage driver 130 may be placed under the stage 120. Specifically, part of a spherical first end of the stage driver 130 may be inserted into the stage 120.

Accordingly, the stage driver 130 can rotate the stage 120 on a horizontal plane and change the slope of the stage 120 in a vertical direction as described in greater detail herein.

A second end of the stage driver 130 may be placed under the stage 120 and shaped like a bar extending in a direction perpendicular to the horizontal plane on which the stage 120 is placed. However, the present inventive concept is not limited thereto. That is, in some embodiments, part of the stage driver 130 placed under the stage 120 can have other shapes and configurations.

The detector 140 may be placed on the stage 120 to be separated from the stage 120. Specifically, the detector 140 may be placed between the stage 120 and the beam irradiating unit 110.

However, the present inventive concept is not limited thereto and, any suitable configuration may be used. For example, in some embodiments, the detector 140 may be placed above or on a side of the beam irradiating unit 110. In addition, in some embodiments of the present inventive concept, the detector 140 may be directly connected to the stage 120. In this case, the detector 140 may be separated from the semiconductor substrate 180 so as to receive a beam reflected by the semiconductor substrate 180.

The detector 140 may receive a beam reflected by the semiconductor substrate 180 and provide the received beam to the amplifier 150. However, the present inventive concept is not limited thereto. That is, for example, in some embodiments, a signal received by the detector 140 may be provided directly to the arithmetic operation unit 170.

The electrode 141 may be placed within the detector 140. The electrode 141 may have a positive (+) charge. When the beam irradiating unit 110 irradiates electrons, the electrode 141 having the positive (+) charge may efficiently induce the electrons having a negative (−) charge and reflected by the semiconductor substrate 180 into the detector 140.

The amplifier 150 may be electrically connected to the detector 140. The amplifier 150 may amplify a signal received from the detector 140 and provide the amplified signal to the imaging unit 160. However, the present inventive concept is not limited thereto. For example, in some embodiments, a signal received by the amplifier 150 may be provided directly to the arithmetic operation unit 170.

Even if a small amount of beam is received by the detector 140, an image of the semiconductor substrate 180 can be obtained efficiently because the signal can be amplified by the amplifier 150.

The imaging unit 160 may be electrically connected to the amplifier 150. The imaging unit 160 may convert a signal received from the amplifier 160 into a 2D image and provide the 2D image to the arithmetic operation unit 170.

The arithmetic operation unit 170 may be electrically connected to the imaging unit 160. The arithmetic operation unit 170 may obtain a 3D image by combining 2D images received from the imaging unit 160.

The arithmetic operation unit 170 may control the stage driver 130. Specifically, the arithmetic operation unit 170 may control the stage driver 130 to rotate the stage 120 on the horizontal plane or change the slope of the stage 120 in the vertical direction. It should be understood that the arithmetic operation unit 170 may be provided as a single unit, or the arithmetic operation unit 170 may be provided by multiple units or processors that perform the operations of the arithmetic operation unit 170 described herein.

The operation of the apparatus 100 for measuring a semiconductor device according to an embodiment of the present inventive concept will now be described with reference to FIGS. 2 through 4.

Figure 2:
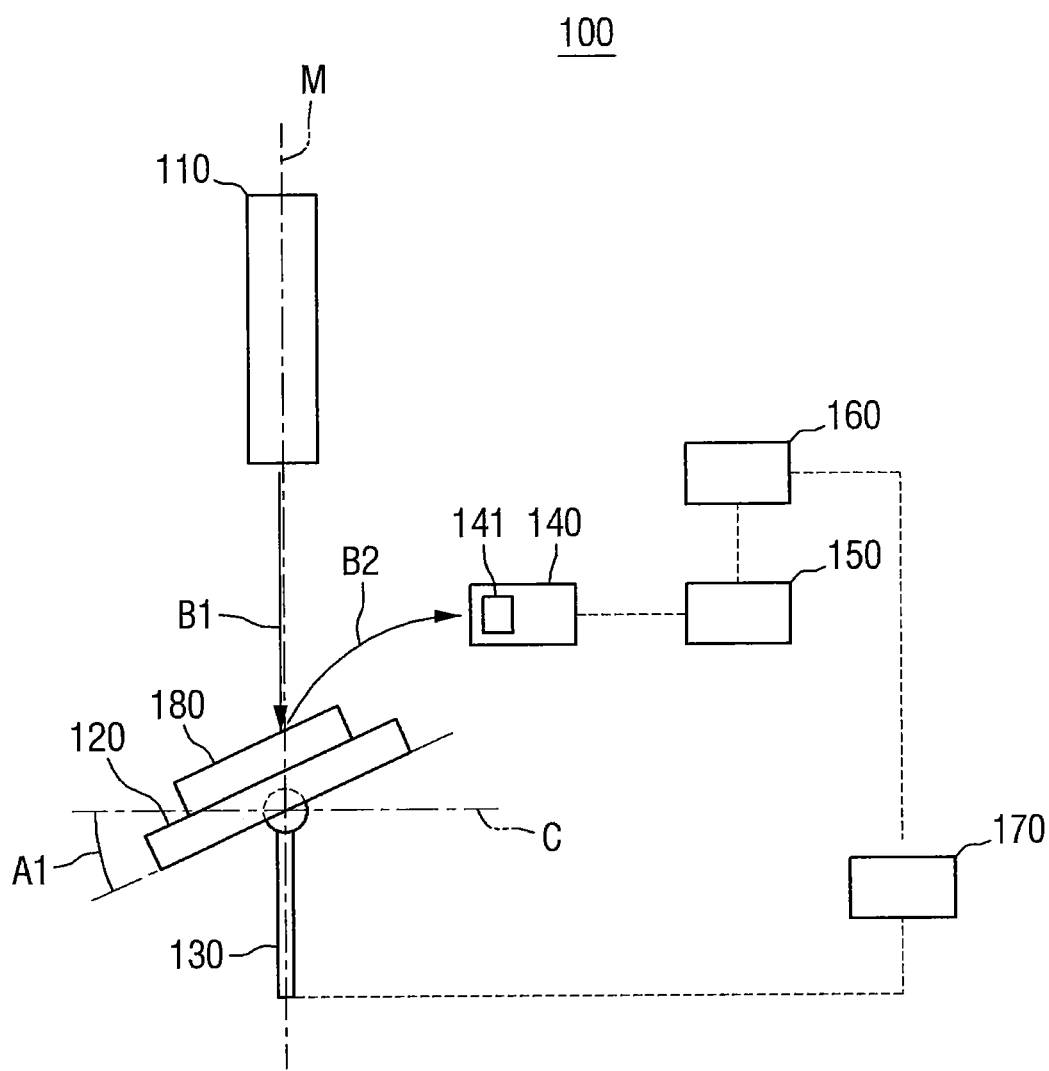
FIGS. 2 and 3 is a schematic diagram of the apparatus illustrating the operation of the apparatus of FIG. 1 according to an embodiment of the present inventive concept.
Figure 3:
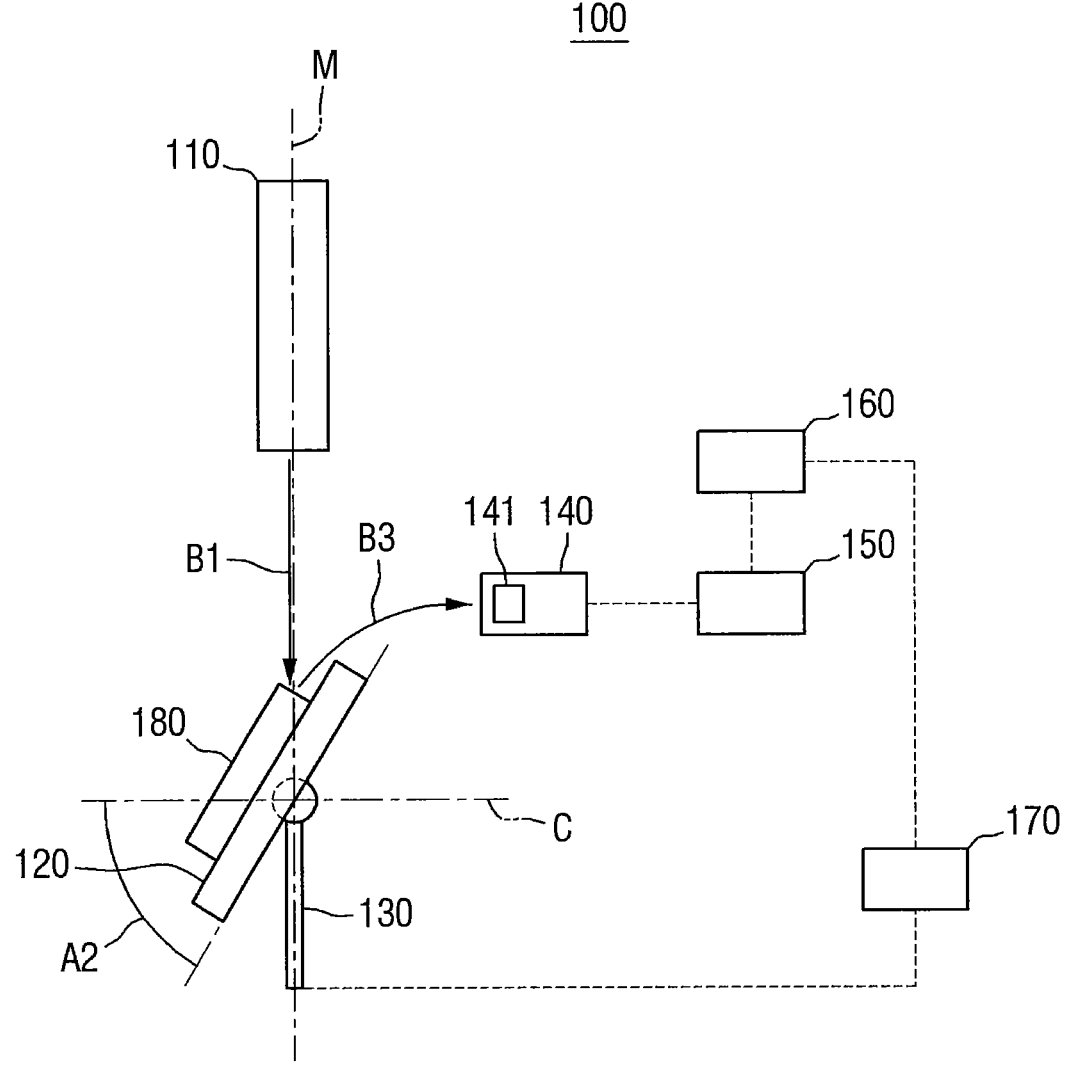

FIGS. 2 and 3 illustrate the operation of the apparatus 100 for measuring a semiconductor device according to an embodiment of the present inventive concept. FIG. 4 illustrates the rotation of the stage 120 on a horizontal plane C according to an embodiment of the present inventive concept.

Referring to FIG. 2, the stage 120 may be rotated toward a central axis M, which is perpendicular to the horizontal plane C lying in the same plane with the stage 120, by a first angle A1 to the horizontal plane C.

The rotation of the stage 120 in the vertical direction can be achieved by the spherical shape of the first end of the stage driver 130. Specifically, the stage 120 can be rotated toward the central axis M by the first angle A1 by the spherical first end of the stage driver 130 which is inserted into the stage 120.

After the stage 120 is rotated toward the central axis M by the first angle A1, a first beam B1 may be irradiated to the semiconductor substrate 180 placed on the stage 120. A second beam B2 generated by the reflection of the first beam B1 off the semiconductor substrate 180 may be received by the detector 140.

When the first and second beams B1 and B2 include electrons, the second beam B2 having a negative (−) charge may be efficiently induced into the detector 140 by the electrode 141 having a positive (+) charge within the detector 140.

Referring to FIG. 3, the stage 120 may be rotated toward the central axis M, which is perpendicular to the horizontal plane C lying in the same plane with the stage 120, by a second angle A2 to the horizontal plane C.

The rotation of the stage 120 in the vertical direction can be achieved by the spherical shape of the first end of the stage driver 130. Specifically, the stage 120 can be rotated toward the central axis M by the second angle A2 by the spherical first end of the stage driver 130 which is inserted into the stage 120.

After the stage 120 is rotated toward the central axis M by the second angle A2, the first beam B1 may be irradiated to the semiconductor substrate 180 placed on the stage 120. A third beam B3 generated by the reflection of the first beam B1 off the semiconductor substrate 180 may be received by the detector 140.

When the first and third beams B1 and B3 include electrons, the third beam B3 having a negative (−) charge may be efficiently induced into the detector 140 by the electrode 141 having a positive (+) charge within the detector 140.

Figure 4:
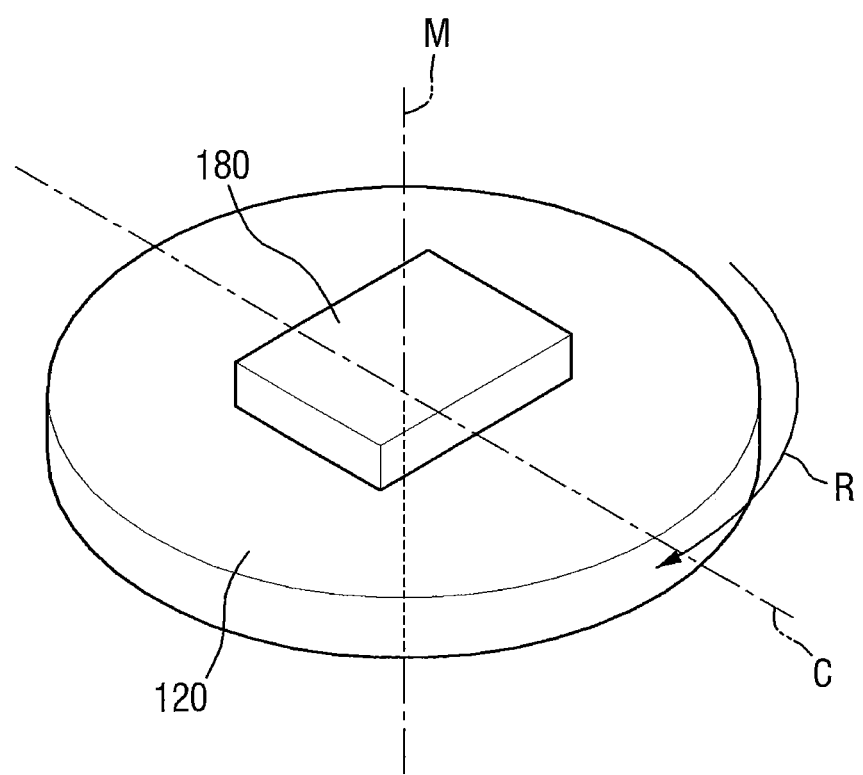
FIG. 4 is a perspective view of the stage of the apparatus of FIG. 2 illustrating the rotation of a stage on a horizontal plane according to an embodiment of the present inventive concept.

Referring to FIG. 4, the stage 120 may be rotated on the horizontal plane C in a clockwise direction R about the central axis M which is perpendicular to the horizontal plane C lying in the same plane with the stage 120. Accordingly, the semiconductor substrate 180 placed on the stage 120 can be rotated. In some embodiments of the present inventive concept, the stage 120 and the semiconductor substrate 180 may be rotated in a counterclockwise direction.

In some embodiments, the stage 120 according to the present inventive concept may be driven on the horizontal plane C in an x-axis direction, a y-axis direction, and a z-axis direction in which the central axis M extends.

The movement of the semiconductor substrate 180 having a plurality of fin structures according to a change in the angle of the stage 120 in embodiments of the present inventive concept will now be described with reference to FIGS. 5 through 7.

Figure 5:
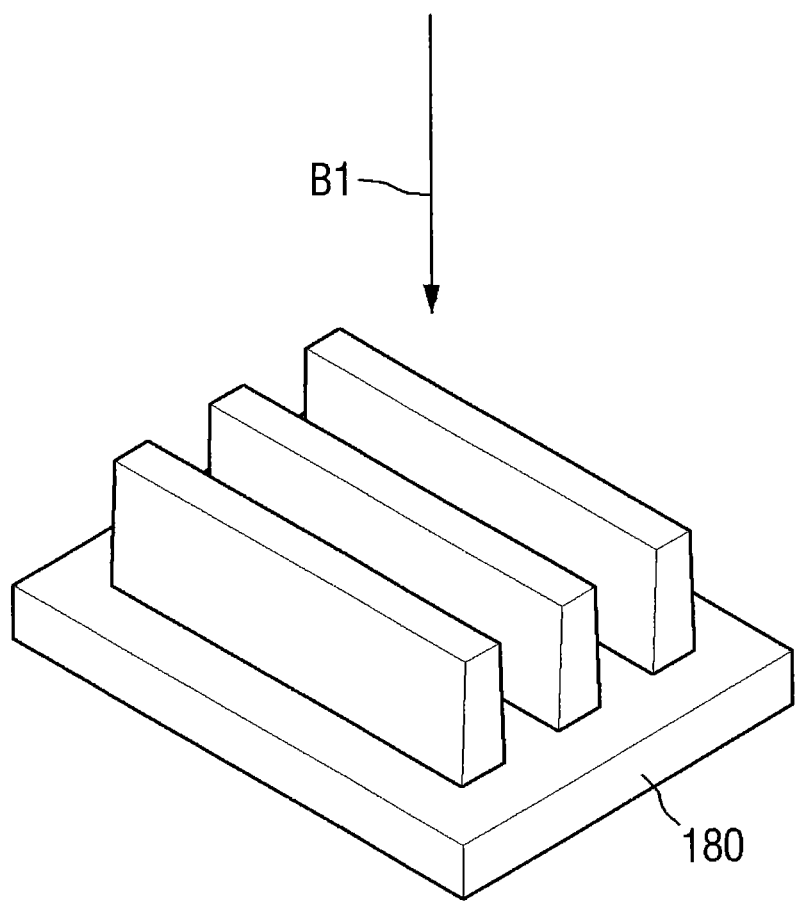
FIGS. 5 through 7 are perspective views illustrating the movement of a semiconductor substrate having a plurality of fin structures according to a change in the angle of the stage in embodiments of the present inventive concept.

Referring to FIG. 5, the semiconductor substrate 180 may be placed in a direction perpendicular to the first beam B1 irradiated from the beam irradiating unit 110. Accordingly, the first beam B1 may be reflected by upper surfaces of the fin structures and an upper surface of the semiconductor substrate 180.

Figure 6:
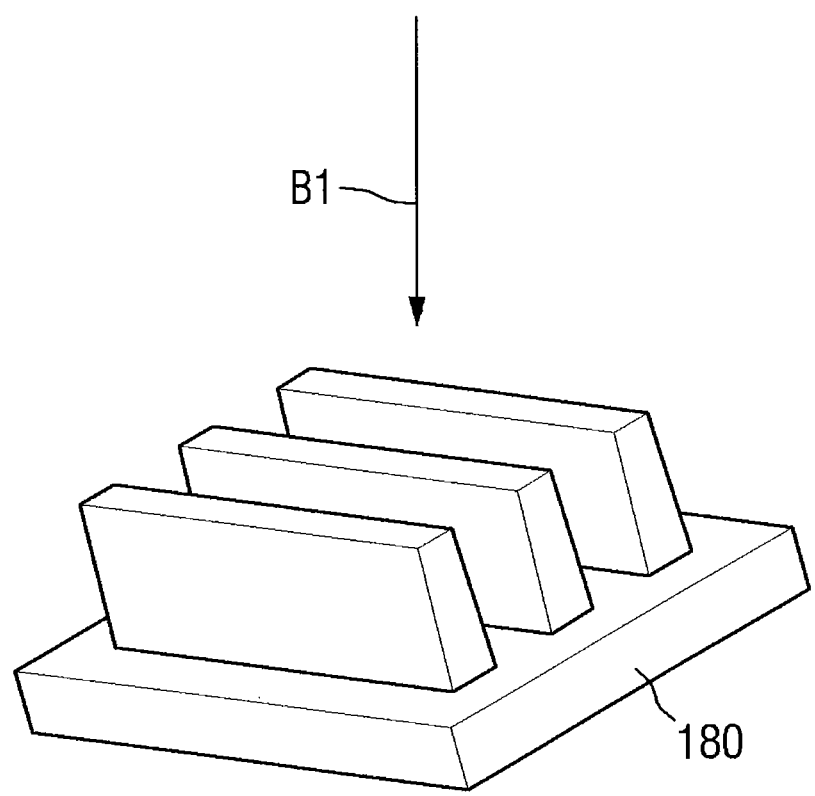

Referring to FIGS. 2 and 6, the stage 120 may be rotated by the first angle A1 to the horizontal plane C such that the semiconductor substrate 180 forms the first angle A1 with the first beam B1 irradiated from the beam irradiating unit 110. Accordingly, the first beam B1 may be reflected by the upper and side surfaces of the fin structures and the upper surface of the semiconductor substrate 180.

Figure 7:
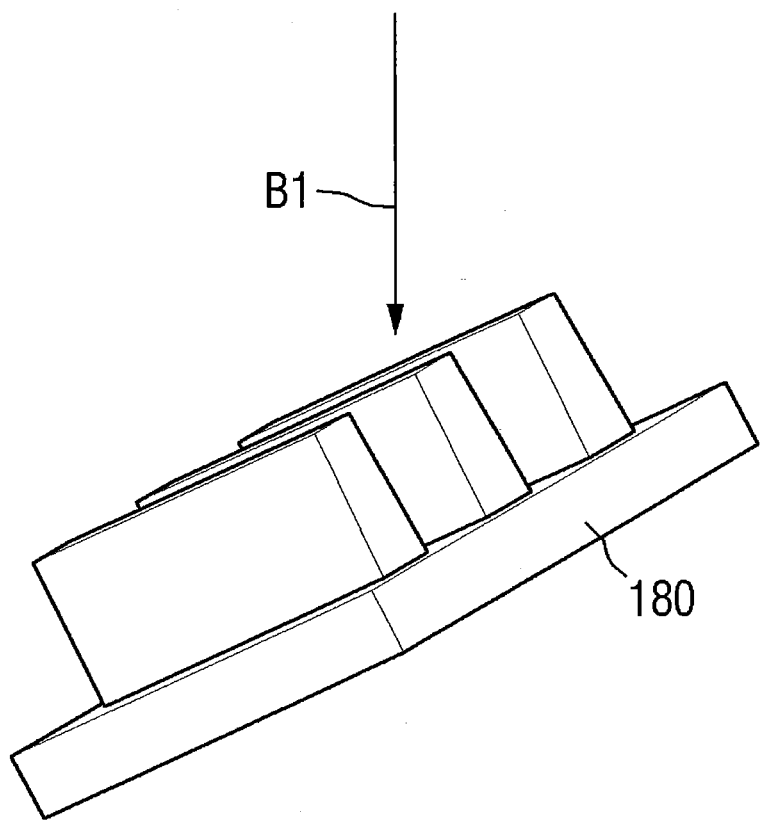

Referring to FIGS. 3 and 7, the stage 120 may be rotated by the second angle A2 to the horizontal plane C such that the semiconductor substrate 180 forms the second angle A2 with the first beam B1 irradiated from the beam irradiating unit 110. Accordingly, the first beam B1 may be reflected by the upper and side surfaces of the fin structures and the upper surface of the semiconductor substrate 180.

The first beam B1 from the beam irradiating unit 110 may be irradiated to all surfaces of the semiconductor substrate 180 having a 3D structure by changing the angle of the semiconductor substrate 180. Specifically, since the first beam B1 is irradiated to the semiconductor substrate 180 placed at a plurality of angles, 2D images of all surfaces of the semiconductor substrate 180 having a 3D structure can be obtained.

A method of measuring a 3D image using the apparatus according to embodiments of the present inventive concept will now be described with reference to FIGS. 8 and 9.

Figure 8:
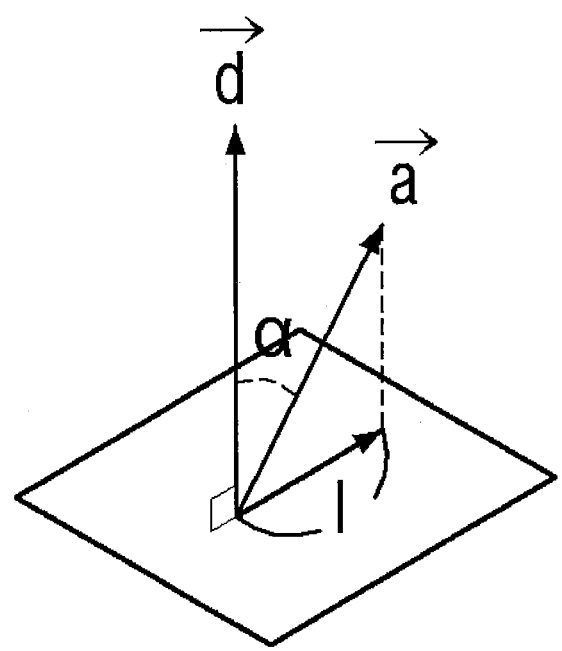
FIG. 8 is a schematic diagram illustrating a measured length and an actual length of a semiconductor substrate according to an incidence angle of a beam in embodiments of the present inventive concept.

FIG. 8 illustrates a measured value and an actual value of a semiconductor substrate according to an incidence angle of a beam in embodiments of the present inventive concept. FIG. 9 is a flowchart sequentially illustrating a method of measuring a 3D image using the apparatus according to embodiments of the present inventive concept.

Referring to FIG. 8, a first beam B1 (d vector) and a calculated value (a vector) of a semiconductor substrate 180 form an angle of α. The calculated value (a vector) of the semiconductor substrate 180 can be obtained as follows using a measured value I of the semiconductor substrate 180 and the angle α:

[Measured value (1)=|calculated value ($a$ vector) |*sin α]

Figure 9:
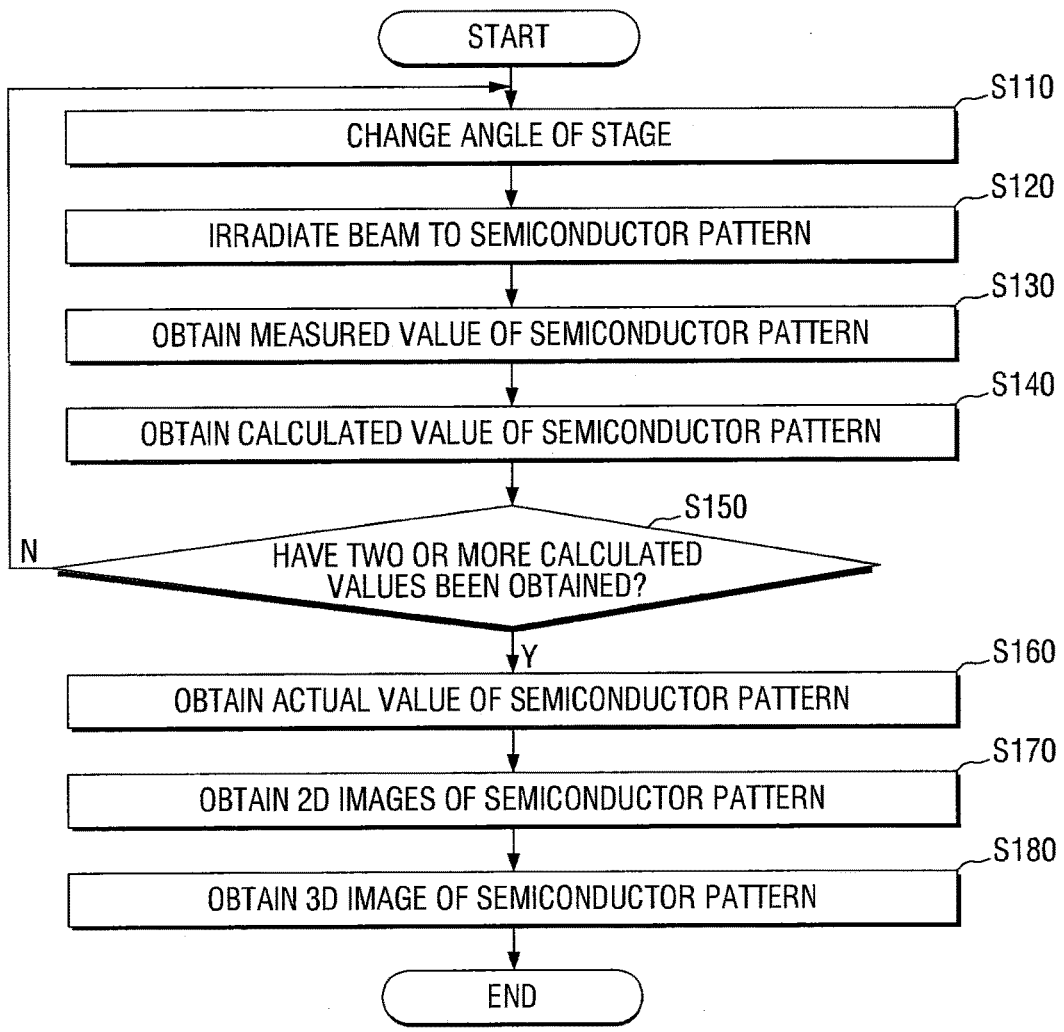
FIG. 9 is a flowchart sequentially illustrating a method of measuring a 3D image using the apparatus according to embodiments of the present inventive concept.

Referring to FIGS. 2, 3 and 9, the stage 120 is rotated toward the central axis M by the first angle A1 to the horizontal plane C (operation S110). Accordingly, the semiconductor substrate 180 placed on the stage 120 may be rotated.

The beam irradiating unit 110 may irradiate a beam B1 to a semiconductor pattern formed on the semiconductor substrate 180 (operation S120). The beam B1 may include electrons.

The beam B1 may be reflected by the semiconductor pattern, and the reflected beam B1 may be received by the detector 140. The beam B1 received by the detector 140 may be converted into a signal and provided accordingly to the arithmetic operation unit 170. The arithmetic operation unit 170 may obtain a first measured value I using the received signal (operation S130).

When the beam B1 includes electrons, the electrons may be efficiently induced into the detector 140 by the electrode 141 placed within the detector 140.

The relationship between an angle α at which the beam B1 is incident upon the semiconductor substrate 180 and the first angle A1 by which the stage 120 is rotated toward the central axis M with respect to the horizontal plane C is as follows:

[α=90−$A1$]

The arithmetic operation unit 170 may calculate a first calculated value (a vector) using the first measured value I and the incidence angle α of the beam B1 (operation S140).

When two or more calculated values (α vectors) have not been obtained, operations S110 through S140 are repeated (operation S150). The stage 120 is rotated toward the central axis M by the second angle A2 to the horizontal plane C (operation S110). Then, operations S120 through S140 may be repeated to calculate a second calculated value (α vector) (operation S140).

When two or more calculated values (α vectors) have been obtained, the arithmetic operation unit 170 may calculate an actual value by calculating a mean value of the first and second calculated values (operation S160).

Then, the arithmetic operation unit 170 may obtain 2D images of the semiconductor pattern using a plurality of calculated actual values (operation S170). In addition, the arithmetic operation unit 170 may obtain a 3D image of the semiconductor pattern by combining the obtained 2D images (operation S180).

In some embodiments, after the stage 120 is rotated toward the central axis M by the first angle A1 to the horizontal plane C, it may be rotated on the same plane with the stage 120 to obtain a plurality of first measured values I.

In addition, the arithmetic operation unit 170 may obtain a plurality of first calculated values (α vectors) using the first angle A1 and the first measured values I. Then, the arithmetic operation unit 170 may obtain a first mean value by calculating a mean value of the first calculated values (α vectors).

Likewise, after the stage 120 is rotated toward the central axis M by the second angle A2 to the horizontal plane C, the arithmetic operation unit 170 may sequentially obtain a plurality of second measured values I, a plurality of second calculated values (α vectors), and a second mean value.

The arithmetic operation unit 170 may calculate an actual value using the first and second mean values.

Consequently, the apparatus 100 for measuring a semiconductor device according to the present inventive concept can obtain a 3D image of the semiconductor pattern using the beam B1 irradiated from the fixed beam irradiating unit 110 by adjusting the slope of the stage 120.

An apparatus for measuring a semiconductor device according to another embodiment of the present inventive concept will now be described with reference to FIG. 10. The apparatus for measuring a semiconductor device according to the current embodiment will hereinafter be described, focusing mainly on differences with the apparatus 100 of FIG. 1.

Figure 10:
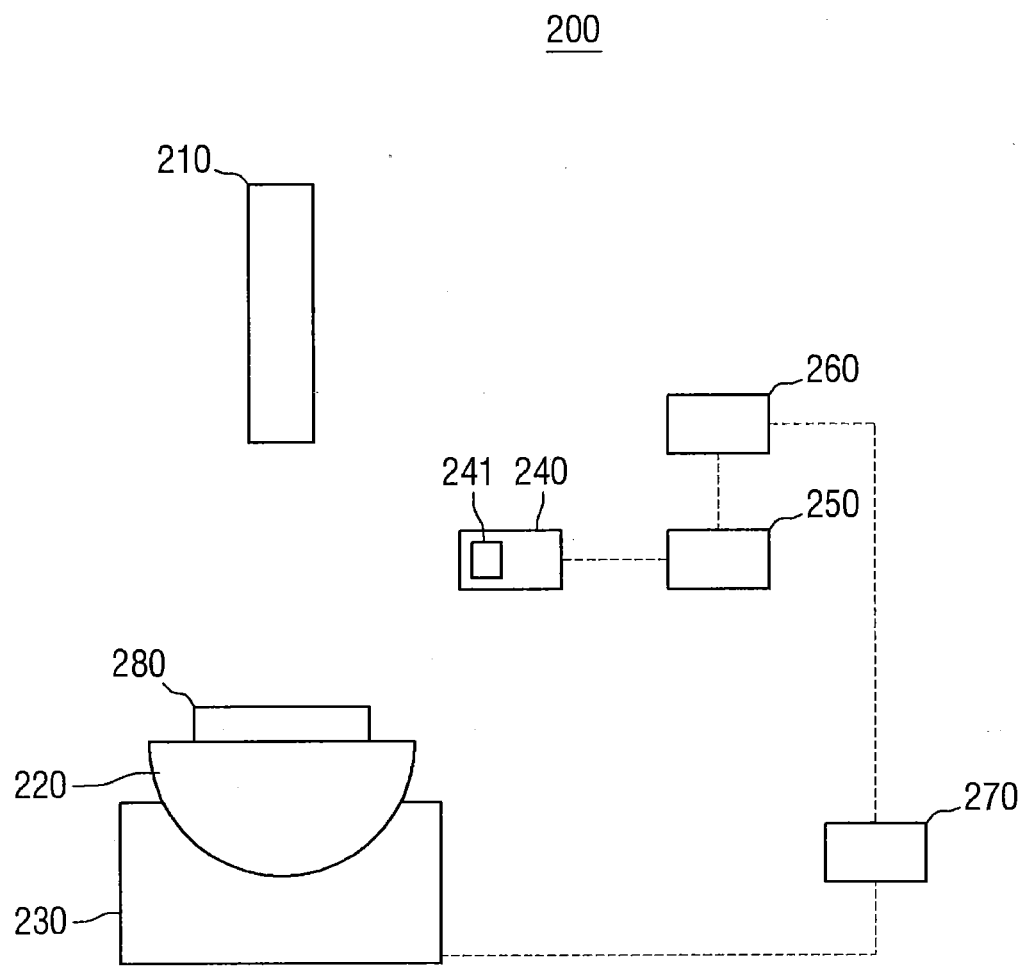
FIG. 10 is a schematic diagram of an apparatus for measuring a semiconductor device according to another embodiment of the present inventive concept.

FIG. 10 illustrates an apparatus 200 for measuring a semiconductor device according to another embodiment of the present inventive concept.

Referring to FIG. 10, the apparatus 200 for measuring a semiconductor device includes a beam irradiating unit 210 and a measuring unit. The measuring unit includes a stage 220, a stage driver 230, a detector 240, an electrode 241, an amplifier 250, an imaging unit 260, and an arithmetic operation unit 270.

Unlike the apparatus 100 of FIG. 1, the apparatus 200 for measuring a semiconductor device includes the hemispherical stage 220. Specifically, the stage 220 has a flat upper surface and a hemispherical lower surface. A semiconductor substrate 280 may be placed on the upper surface of the stage 220.

In addition, the stage driver 230 may partially cover a lower part of the stage 220. Specifically, a part of an upper surface of the stage driver 230 may be concave, and part of the hemispherical lower part of the stage 220 may be placed on the concave part of the upper surface of the stage driver 230.

The operation of the apparatus 200 for measuring a semiconductor device according to another embodiment of the present inventive concept will now be described with reference to FIGS. 11 through 13. The operation of the apparatus 200 for measuring a semiconductor device according to the current embodiment will hereinafter be described, focusing mainly on differences with the operation of the apparatus 100 of FIG. 1.

Figure 11:
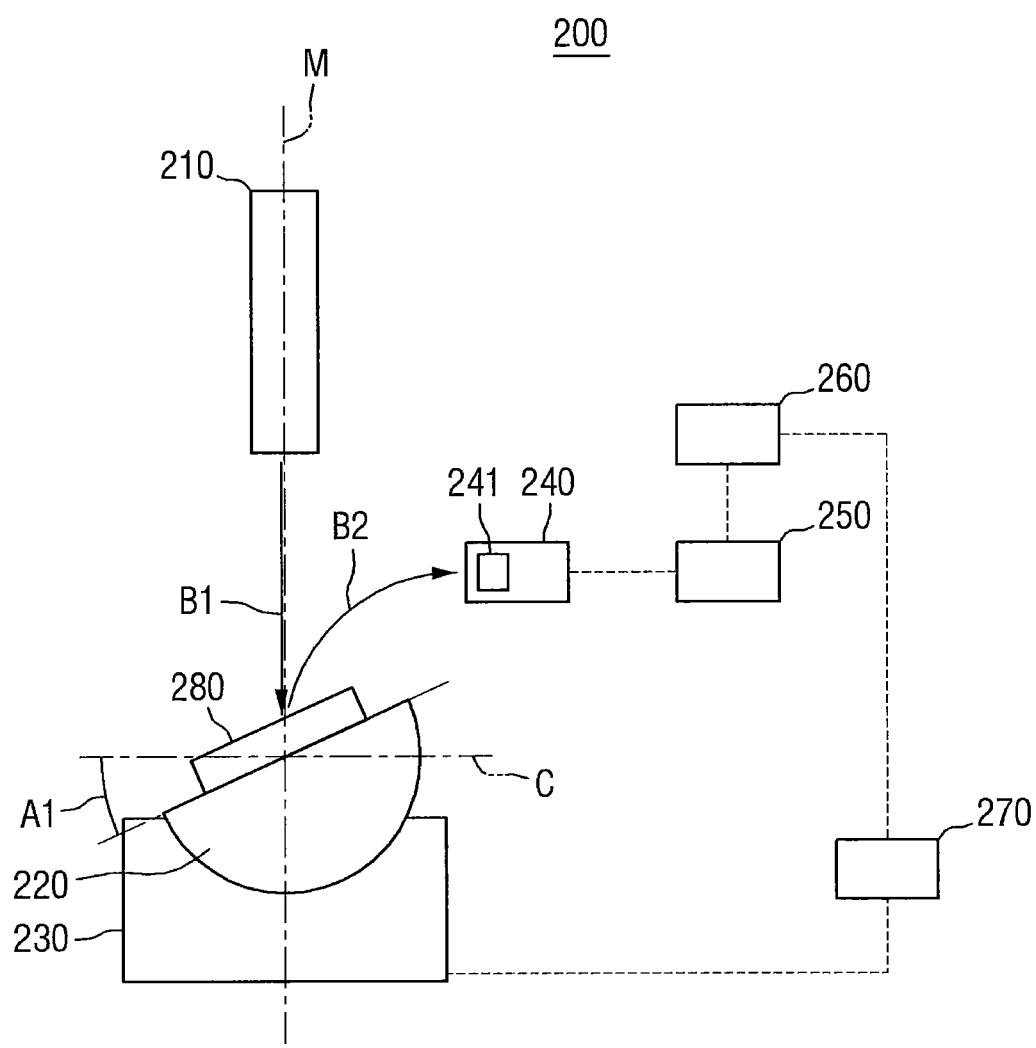
FIGS. 11 and 12 is a schematic diagram illustrating the operation of the apparatus of FIG. 10 according to another embodiment of the present inventive concept.
Figure 12:
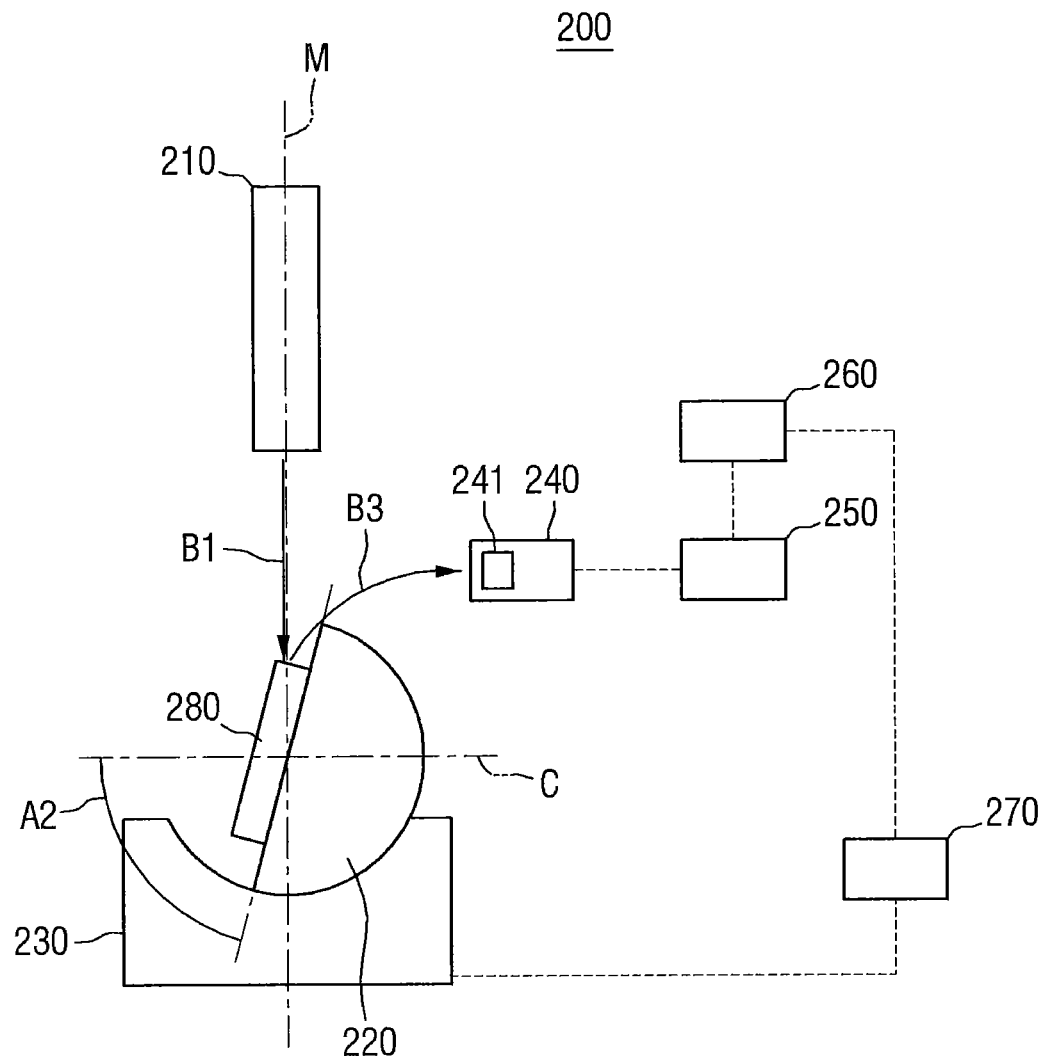

FIGS. 11 and 12 illustrate the operation of the apparatus 200 for measuring a semiconductor device according to another embodiment of the present inventive concept. FIG. 13 illustrates the rotation of the stage 220 on a horizontal plane C according to another embodiment of the present inventive concept.

Referring to FIGS. 11 and 12, unlike in the apparatus 100 of FIG. 1, in the apparatus 200 for measuring a semiconductor device, the lower surface of the stage 220 may be driven in contact with the upper surface of the stage driver 230. Specifically, the stage driver 230 may be connected to the lower surface of the stage 220 so as to drive the stage 220.

Accordingly, the stage 220 can be rotated toward a central axis M, which is perpendicular to the horizontal plane C lying in the same plane with the stage 220, by a first or second angle A1 or A2 to the horizontal plane C.

Figure 13:
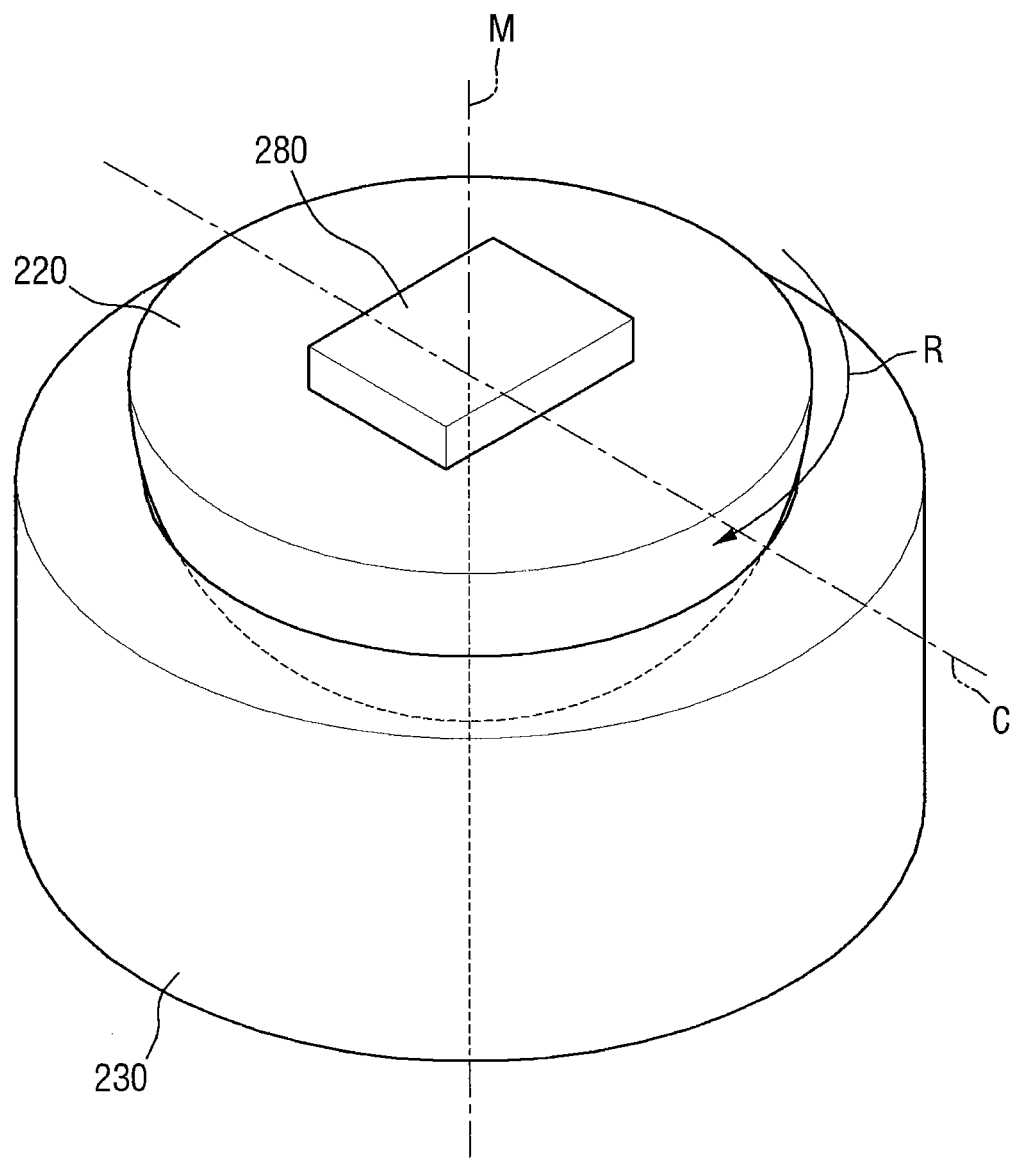
FIG. 13 is a perspective view of the stage of the apparatus of FIG. 10 illustrating the rotation of a stage on a horizontal plane according to another embodiment of the present inventive concept.

Referring to FIG. 13, the stage driver 230 connected to the lower surface of the stage 220 may rotate the stage 220 on the horizontal plane C in a clockwise direction R about the central axis M which is perpendicular to the horizontal plane C lying in the same plane with the stage 220.

Since a contact surface of the stage 220 and the stage driver 230 is relatively increased in the apparatus 200 for measuring a semiconductor device as compared with the apparatus of FIG. 100 of FIG. 1, the apparatus 200 can stably drive the stage 220.

An apparatus for measuring a semiconductor device according to another embodiment of the present inventive concept will now be described with reference to FIGS. 14 and 15. The apparatus for measuring a semiconductor device according to the current embodiment will hereinafter be described, focusing mainly on differences with the apparatus 100 of FIG. 1.

Figure 14:
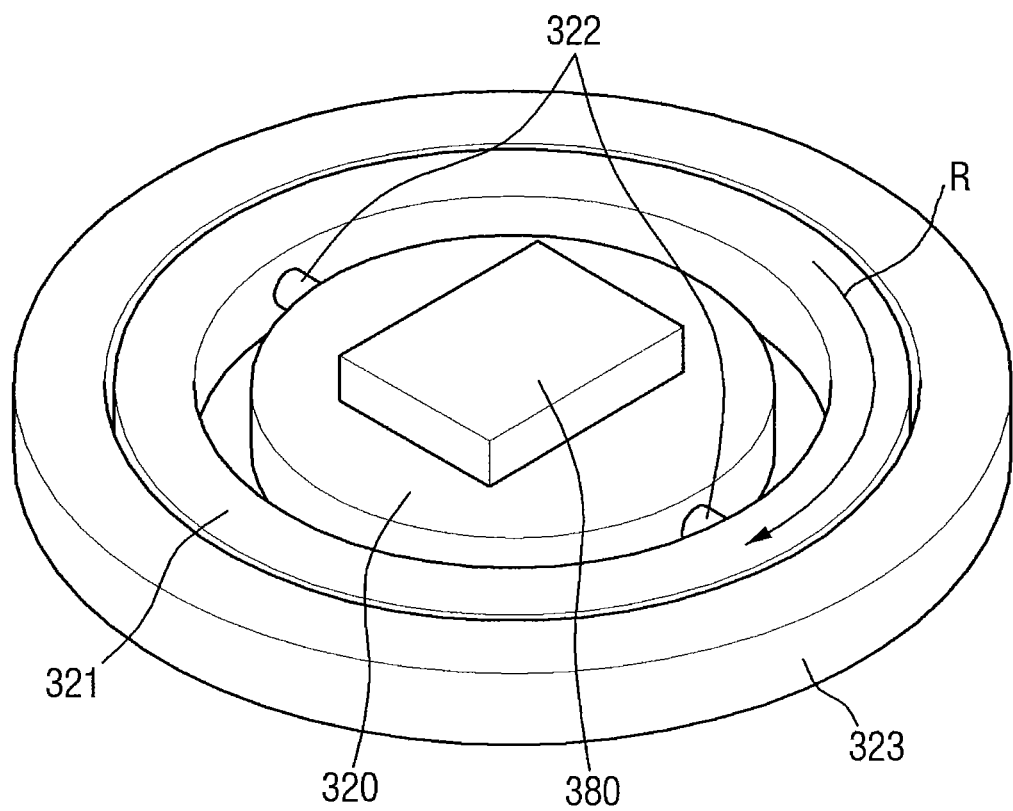
FIG. 14 is a perspective view of a stage and peripheral devices of an apparatus for measuring a semiconductor device according to another embodiment of the present inventive concept.

FIG. 14 illustrates a stage 320 and peripheral devices of an apparatus 300 for measuring a semiconductor device according to another embodiment of the present inventive concept. FIG. 15 illustrates the operation of the stage 320 according to another embodiment of the present inventive concept.

Referring to FIG. 14, the apparatus 300 for measuring a semiconductor device includes the stage 320, an angle adjuster 321, stage connectors 322, and a diffraction adjuster 323.

Unlike the apparatus 100 of FIG. 1, the apparatus 300 for measuring a semiconductor device further includes the angle adjuster 321, the stage connectors 322, and the diffraction adjuster 323.

A semiconductor substrate 380 may be placed on the stage 320. The angle adjuster 321 may lie in the same plane with the stage 320 to surround a side surface of the stage 320.

The stage connectors 322 may connect the side surface of the stage 320 and the angle adjuster 321. Specifically, an end of each of the stage connectors 322 may be connected to the side surface of the stage 320, and the other end of each of the stage connectors 322 may be connected to the angle adjuster 321.

The stage connectors 322 may be disposed on both sides of the stage 320, respectively, and may lie on the same straight line. The stage 320 may be rotated about the stage connectors 322 by the angle adjuster 321.

The diffraction adjuster 323 may lie in the same plane with the angle adjuster 321 to surround a side surface of the angle adjuster 321. The diffraction adjuster 323 may be connected to the side surface of the angle adjuster 321 so as to rotate the angle adjuster 321 in a clockwise direction R. Accordingly, the semiconductor substrate 380 placed on the stage 320 may be rotated. However, in some other embodiments, the stage 320 and the semiconductor substrate 380 may be rotated in a counterclockwise direction.

Figure 15:
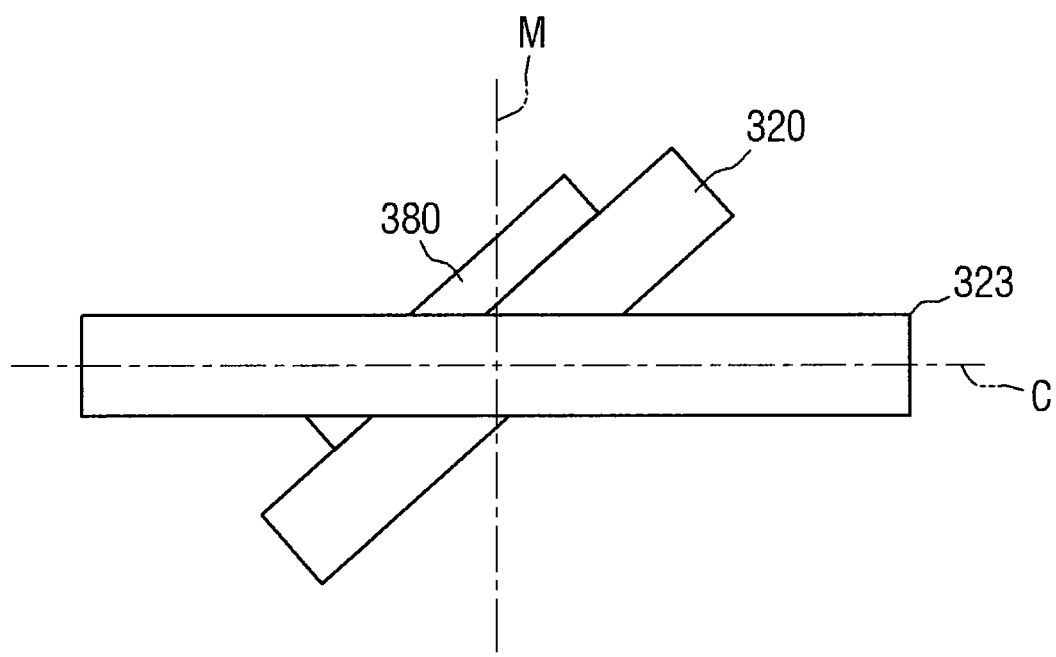
FIG. 15 is a side schematic view of the stage of FIG. 14 illustrating the operation of the stage of FIG. 14 according to another embodiment of the present inventive concept.

Referring to FIGS. 14 and 15, the stage 320 may be rotated about an axis, i.e., the stage connectors 322 toward a central axis M from a horizontal plane C in which the angle adjuster 321 is placed.

Unlike in the apparatus 100 of FIG. 1, in the apparatus 300 for measuring a semiconductor device, a device for changing the angle of the stage 320 in a vertical direction and a device for rotating the stage 320 on the horizontal plane C are separated. Accordingly, the apparatus 300 can improve the precision of driving the stage 320.

Figure 16:
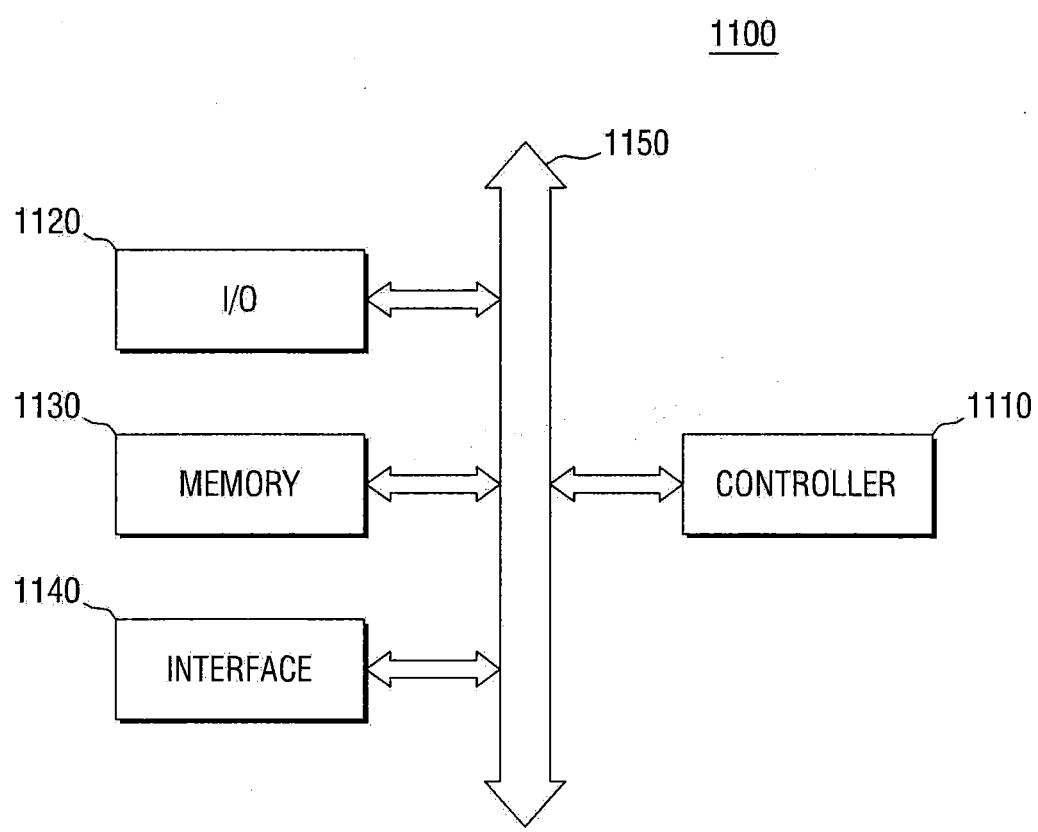
FIG. 16 is a block diagram of an electronic system including a semiconductor apparatus formed using an apparatus for measuring a semiconductor device according to embodiments of the present inventive concept.

FIG. 16 is a block diagram of an electronic system 1100 including a semiconductor apparatus formed using an apparatus for measuring a semiconductor device according to embodiments of the present inventive concept.

Referring to FIG. 16, the electronic system 1100 may include a controller 1110, an input/output (I/O) device 1120, a memory device 1130, an interface 1140 and a bus 1150.

The controller 1110, the I/O device 1120, the memory device 1130 and/or the interface 1140 may be connected to one another by the bus 1150. The bus 1150 may serve as a path for transmitting data.

The controller 1110 may include at least one of a microprocessor, a digital signal processor, a microcontroller and logic devices capable of performing similar functions to those of a microprocessor, a digital signal processor and a microcontroller.

The I/O device 1120 may include a keypad, a keyboard and a display device. The memory device 1130 may store data and/or commands.

The interface 1140 may be used to transmit data to or receive data from a communication network. The interface 1140 may be a wired or wireless interface. In an example, the interface 1140 may include an antenna or a wired or wireless transceiver. The electronic system 1100 may further include a high-speed dynamic random access memory (DRAM) or static random access memory (SRAM) as a working memory for improving the operation of the controller 1110.

A semiconductor apparatus manufactured according to embodiments of the present inventive concept may be provided in the memory device 1130 or in the controller 1110 or the I/O device 1120.

The electronic system 1100 may be applied to nearly all types of electronic products capable of transmitting and/or receiving information in a wireless environment, such as a personal data assistant (PDA), a portable computer, a web tablet, a wireless phone, a mobile phone, a digital music player, a memory card, etc.

While the present inventive concept has been particularly shown and described with reference to example embodiments thereof, it will be understood by those of ordinary skill in the art that various changes in form and detail may be made therein without departing from the spirit and scope of the present inventive concept as defined by the following claims. The example embodiments should be considered in a descriptive sense only and not for purposes of limitation.

What is claimed is:

1. An apparatus for measuring a semiconductor device, the apparatus comprising:
   a beam irradiating unit configured to irradiate a first beam to a semiconductor substrate;
   a stage configured to receive the semiconductor substrate thereon and which is configured to rotate toward a central axis, which is perpendicular to a horizontal plane lying in the same plane with the semiconductor substrate, by a first angle to the horizontal plane and a second angle that is different from the first angle;
   a detector configured to receive a second beam generated by reflecting the first beam to the semiconductor substrate at the first angle and to receive a third beam generated by reflecting the first beam to the semiconductor substrate at the second angle;
   an arithmetic operation unit configured to generate a 3D image of the semiconductor substrate using the second beam and the third beam received by the detector; and
   an angle adjuster which lies in the horizontal plane and is positioned around a perimeter of a side surface of the stage and is connected to the stage so as to rotate the stage toward the central axis by the first and second angles.

2. The apparatus of claim 1, further comprising a stage driver having a spherical first end inserted into the stage and a second end disposed under the stage in a direction in which the central axis extends.

3. The apparatus of claim 2, wherein the stage driver is configured to rotate the stage toward the central axis by the first and second angles to the horizontal plane.

4. The apparatus of claim 3, wherein the arithmetic operation unit is configured to control the stage driver.

5. The apparatus of claim 1, wherein the stage comprises a flat upper surface and a hemispherical lower surface and further comprising a stage driver adjacent a lower surface of the stage and that is configured to rotate the stage toward the central axis by the first and second angles to the horizontal plane.

6. The apparatus of claim 5, wherein the stage driver is configured to rotate the stage about the central axis on the horizontal plane.

7. The apparatus of claim 1, further comprising a diffraction adjuster which lies in the same plane with the angle adjuster and is positioned around a perimeter of a side surface of the angle adjuster and is connected to the angle adjuster so as to rotate the stage about the central axis on the horizontal plane.

8. The apparatus of claim 1, wherein the second and third beams comprise electrons, and the detector comprises an electrode which induces the electrons toward the detector.

9. An apparatus for measuring a semiconductor device, the apparatus comprising:
   a beam irradiating unit; and
   a measuring unit configured to measure a structure of a semiconductor pattern placed on a stage using first and second beams irradiated from the beam irradiating unit, wherein the measuring unit rotates the stage toward a central axis, which is perpendicular to a horizontal plane lying in the same plane with the stage, by a first angle to the horizontal plane, obtains a first measured value of the semiconductor pattern by irradiating the first beam to the semiconductor pattern, rotates the stage toward the central axis by a second angle different from the first angle to the horizontal plane, and obtains a second measured value of the semiconductor pattern by irradiating the second beam to the semiconductor pattern, wherein the stage is configured to rotate on the same plane with the stage rotated by the first angle to the horizontal plane and is rotated on the same plane with the stage rotated by the second angle to the horizontal plane, and the measuring unit comprising an arithmetic operation unit configured to obtain a plurality of first calculated values using the first angle and a plurality of first measured values obtained by rotating the stage on the same plane with the stage at the first angle, to obtain a first mean value using the first calculated values, to obtain a plurality of second calculated values using the second angle and a plurality of second measured values obtained by rotating the stage on the same plane with the stage at the second angle, to obtain a second mean value using the second calculated values, and to calculate an actual value using the first mean value and the second mean value.

10. The apparatus of claim 9, wherein the measuring unit comprises a detector configured to detect the first and second beams reflected by the semiconductor pattern to obtain each first measured value of the plurality of first measured values and each second measured value of the plurality of second measured values.

11. The apparatus of claim 9, wherein the arithmetic operation unit obtains 2D images of the semiconductor pattern by combining a plurality of actual values and obtains a 3D image of the semiconductor pattern by combining the 2D images.

12. An apparatus for measuring a semiconductor device, the apparatus comprising:
 a beam irradiating unit configured to irradiate a beam to a semiconductor substrate that is reflected as a reflected beam from the semiconductor substrate;
 a stage configured to receive the semiconductor substrate thereon and configured to rotate toward a central axis, which is perpendicular to a horizontal plane lying in the same plane with the semiconductor substrate;
 a detector configured to detect the reflected beam from the semiconductor substrate; and
 an arithmetic operation unit configured to control a rotation of the stage such that two or more reflected beams are detected by the detector at two or more respective different angles, wherein the arithmetic operation unit is configured to generate two or more calculated values corresponding to the two or more reflected beams using the two or more respective different angles, and to generate an actual value using a mean value of the two or more calculated values.

13. The apparatus of claim 12, wherein the arithmetic operation unit is configured to generate a 3D image of the semiconductor substrate using the two or more reflected beams detected by the detector.

14. The apparatus of claim 12, wherein the arithmetic operation unit obtains 2D images of the semiconductor substrate by combining a plurality of actual values and obtains a 3D image of the semiconductor substrate by combining the 2D images.

15. The apparatus of claim 12, wherein the irradiated beam and the two or more reflected beams comprise electrons, and the detector comprises an electrode which induces the electrons toward the detector.

* * * * *